United States Patent [19]

Huellmann et al.

[11] Patent Number: 5,068,479
[45] Date of Patent: Nov. 26, 1991

[54] PREPARATION OF 1,1,3,4,4,6-HEXAMETHYL-1,2,3,4-TETRA-HYDRONAPHTHALENE

[75] Inventors: Michael Huellmann, Heppenheim; Herbert Mayr, Gross Groenau; Rainer Becker, Bad Duerkheim, all of Fed. Rep. of Germany

[73] Assignee: BASF Aktiengesellschaft, Ludwigshafen, Fed. Rep. of Germany

[21] Appl. No.: 668,484

[22] Filed: Mar. 13, 1991

[30] Foreign Application Priority Data

Mar. 17, 1990 [DE] Fed. Rep. of Germany ....... 4008694

[51] Int. Cl.$^5$ .............................................. C07C 5/00
[52] U.S. Cl. .................................... 585/411; 585/410
[58] Field of Search ............................... 585/410, 411

[56] References Cited

U.S. PATENT DOCUMENTS

| | | | |
|---|---|---|---|
| 2,759,022 | 8/1956 | Fuchs | 568/335 |
| 2,851,501 | 9/1958 | Benz et al. | 585/410 |
| 3,246,044 | 4/1966 | Wood et al. | 585/409 |
| 3,278,621 | 10/1966 | Stofberg et al. | 585/408 |
| 3,379,782 | 4/1968 | Kahn | 585/411 |
| 3,379,783 | 4/1968 | Kahn | 585/410 |
| 3,379,785 | 4/1968 | Kahn | 585/410 |
| 3,856,875 | 12/1974 | Wood et al. | 585/410 |
| 4,284,818 | 8/1981 | Sato et al. | 568/323 |
| 4,551,573 | 11/1985 | Cobb | 585/459 |
| 4,877,910 | 10/1989 | Frank | 585/411 |
| 4,877,916 | 10/1989 | Frank | 585/411 |

Primary Examiner—Curtis R. Davis
Attorney, Agent, or Firm—John H. Shurtleff

[57] ABSTRACT

A process for preparing 1,1,3,4,4,6-hexamethyl-1,2,3,4-tetrahydronaphthalene of the formula I

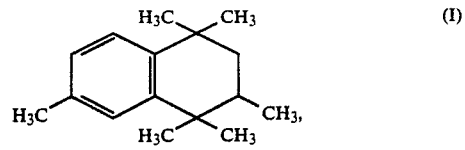

comprises reacting p-cymene of the formula II

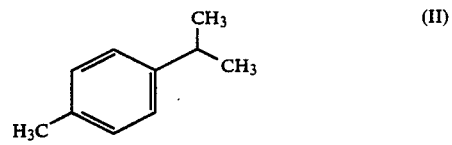

with a hexene of the formula IIIa, IIIb and/or IIIc

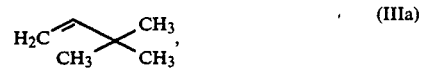

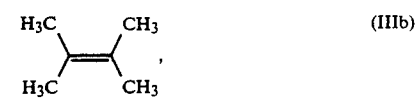

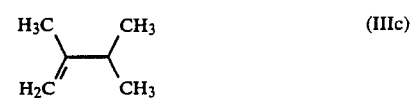

in the presence of a catalytic amount of aluminum halide and a catalytic amount of a triphenylmethyl compound of the formula IV

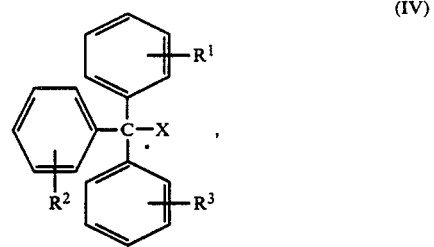

wherein $R^1$, $R^2$ and $R^3$ are each, independently of one another, hydrogen, $C_1$–$C_4$-alkyl, nitro or halogen and X is hydrogen or halogen.

6 Claims, No Drawings

PREPARATION OF 1,1,3,4,4,6-HEXAMETHYL-1,2,3,4-TETRAHYDRONAPHTHALENE

The present invention relates to a novel and improved process for the preparation of 1,1,3,4,4,6-hexamethyl-1,2,3,4-tetrahydronaphthalene (1,1,3,4,4,6-hexamethyltetralin) by reacting p-cymene with certain hexene isomers in the presence of catalytic amounts of an aluminum halide and catalytic amounts of a triphenylmethyl compound.

Acetylation of 1,1,3,4,4,6-hexamethyl-1,2,3,4-tetrahydronaphthalene results in an extremely valuable tetralin musk, i.e. 7-acetyl-1,1,3,4,4,6-hexamethyl-1,2,3,4-tetrahydronaphthalene (Tonalid®). This compound is of great importance as an artificial musk, particularly because of its high quality and persistent fragrance. The substance is furthermore suitable, by reason of its sweetish note, as a substitute for the nitro musks which will presumably have to be replaced for toxicological reasons.

U.S. Pat. No. 2,759,022 discloses the reaction of p-cymene with methyl-tert-butylcarbinol in the presence of a sulfuric acid catalyst. The reaction product is not characterized in terms of its structural formula, nor are details of the yield given.

U.S. Pat. No. 2,851,501, U.S. Pat. No. 3,246,044, U.S. Pat. No. 3,278,621, U.S. Pat. No. 3,379,785 and NL-A 66 12 053 disclose the preparation of 1,1,3,4,4,6-hexamethyl-1,2,3,4-tetrahydronaphthalene and 7-acetyl-1,1,3,4,4,6-hexamethyl-1,2,3,4-tetrahydronaphthalene via α,p-dimethylstyrene V

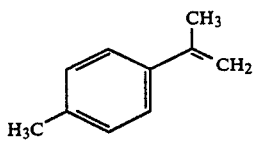

The disadvantage of this process is that the α,p-dimethylstyrene which is needed must be prepared from p-cymene.

U.S. Pat. No. 3,856,875 and DE-A 29 10 493 disclose the synthesis of 1,1,3,4,4,6-hexamethyl-1,2,3,4-tetrahydronaphthalene by reaction of p-cymene and neohexene or 2,3-dimethyl-1-butene and a tert-alkyl halide in the presence of an aluminum halide catalyst. The disadvantage of these processes is, in particular, the use of equimolar amounts of halogenated compounds such as tert-butyl chloride or ethylene dichloride. In addition, the cycloalkylation results in equimolar amounts of gaseous hydrogen chloride which makes special precautionary measures necessary.

U.S. Pat. No. 4,551,573 discloses a process in which satisfactory yields of 1,1,3,4,4,6-hexamethyl-1,2,3,4-tetrahydronaphthalene are obtained from p-cymene and neohexene when catalytic amounts of iodine are used. However, this process is also unsuitable for industrial application because the use of iodine involves great problems (iodine toxicity, corrosion of systems, unwanted coloration of products and elaborate working up).

It is an object of the present invention to remedy the abovementioned disadvantages.

We have found that this object is achieved by a novel and improved process for preparing 1,1,3,4,4,6-hexamethyl-1,2,3,4-tetrahydronaphthalene of the formula I

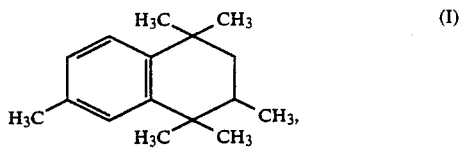

which comprises reacting p-cymene of the formula II

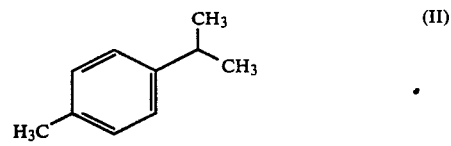

with a hexene of the formula IIIa, IIIb and/or IIIc

in the presence of a catalytic amount of aluminum halide and a catalytic amount of a triphenylmethyl compound of the formula IV

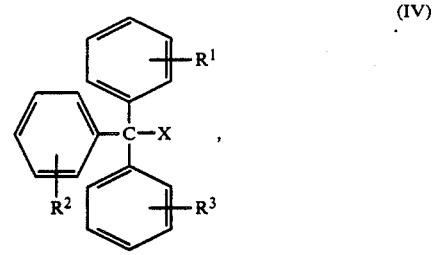

where $R^1$, $R^2$ and $R^3$ are each, independently of one another, hydrogen, $C_1$–$C_4$-alkyl, nitro or halogen and X is hydrogen or halogen.

The process for the preparation of 1,1,3,4,4,6-hexamethyl-1,2,3,4-tetrahydronaphthalene I can be carried out as follows:

p-cymene (II) and the aluminum halide and triphenylmethyl compound (IV) as catalysts are introduced first, and the hexene (IIIa, IIIb or IIIc) is added.

The reaction is carried out at from −10° to 50° C., preferably from 10° to 40° C., particularly preferably from 15° to 30° C. The reaction can be carried out in the presence of a solvent such as $C_5$–$C_{20}$-alkane, e.g. pentane, hexane, cyclohexane or in the absence of a solvent, preferably without solvent.

Examples of suitable aluminum halides are aluminum trichloride, tribromide and triiodide. Anhydrous aluminum trichloride, tribromide or triiodide is preferably used, particularly preferably anhydrous aluminum trichloride.

Examples of suitable triphenylmethyl compounds IV are triphenylmethyl chloride, 3,3',3''-trichlorotriphenylmethyl chloride, 4,4',4''-trichlorotriphenylmethyl chloride, preferably 3,3',3''-trichlorotriphenylmethyl chloride, particularly preferably triphenylmethyl chloride. The preparation of, for example, triphenylmethyl chloride is to be found, for example, in Beilstein, Vol. 5, p. 700 or in Organikum, VEB Verlag 1977, p. 399.

In general, the aluminum halide and p-cymene are used in the molar ratio of from 0.001:1 to 0.5:1, preferably 0.005:1 to 0.2:1, particularly preferably 0.05:1 to 0.1:1, and the triphenylmethyl compound and p-cymene are in the molar ratio of from 0.001:1 to 0.1:1, preferably 0.005:1 to 0.04:1, particularly preferably 0.05:1 to 0.02:1.

The 1,1,3,4,4,6-hexamethyl-1,2,3,4-tetrahydronaphthalene obtained by the novel process can be acylated in a conventional manner (U.S. Pat. No. 3,246,044, Example II) to give the tetralin musk 7-acetyl-1,1,3,4,4,6-hexamethyl-1,2,3,4-tetrahydronaphthalene.

EXAMPLES

EXAMPLE 1

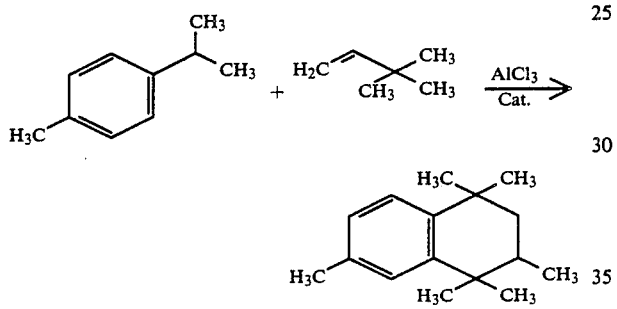

7 g (0.052 mol) of anhydrous aluminum trichloride and 2.78 g (0.01 mol) of triphenylmethyl chloride are added to 90 g (0.67 mol) of p-cymene at room temperature (20° to 25° C.). Then, over the course of 9 minutes, 85 g (1.01 mol) of neohexene are added dropwise in such a way that the mixture is maintained at from 30° to 35° C. Immediately after this addition, a sample is taken for analysis by gas chromatography. Six further samples are taken at 10 minute intervals for investigation by gas chromatography. The results are compiled in Table 1.

TABLE 1

Preparation of 1,1,3,4,4,6-hexamethyl-1,2,3,4-tetrahydronaphthalene from p-cymene and neohexene

| Reaction time (min) | Conversion (%) | | | Selectivity (%) | | |
|---|---|---|---|---|---|---|
| | AlCl$_3$ + (C$_6$H$_5$)$_3$CCl | AlCl$_3$ + I$_2$* | AlCl$_3$ | AlCl$_3$ + (C$_6$H$_5$)$_3$CCl | AlCl$_3$ + I$_2$* | AlCl$_3$ |
| 8 | 80 | 82 | 47 | 77 | 75 | 73 |
| 18 | 81 | 82 | 56 | 76 | 75 | 73 |
| 28 | 82 | 83 | 57 | 76 | 74 | 73 |
| 38 | 83 | 83 | 64 | 76 | 74 | 72 |
| 48 | 83 | 83 | 69 | 76 | 74 | 72 |
| 58 | 83 | 83 | 72 | 74 | 74 | 72 |

*US-A 4 551 573

EXAMPLE 2

17.5 g (0.13 mol) of aluminum trichloride and 8.4 g (0.03 mol) of triphenylmethyl chloride are added to 335 g of p-cymene (2.5 mol) at room temperature (20° to 25° C.). Then, over the course of 45 min, 420 g (5.0 mol) of neohexene are added dropwise in such a way that the temperature does not exceed about 35° C. Hydrolysis is carried out immediately after this addition, the organic phase is filtered off, washed with water and dried with Na$_2$SO$_4$, and then remaining p-cymene and low boilers are removed from the required product by distillation. The residue contains 520 g of 1,1,3,4,4,6-hexamethyl-1,2,3,4-tetrahydronaphthalene (61%). This corresponds to a yield of 59% based on p-cymene.

EXAMPLE 3

Reaction of p-cymene with 2,3-dimethyl-1-butene and triphenylmethyl chloride 2.1 g (0.016 mol) of AlCl$_3$ and 1.0 g (3.6 mmol) of triphenylmethyl chloride are added to 40.2 g of p-cymene (0.3 mol) at room temperature. Then, over the course of 5 minutes, 50.4 g (0.6 mol) of 2,3-dimethyl-1-butene are added dropwise (exothermic reaction) and hydrolysis is carried out immediately after this addition. Working up in a similar manner to Example 1 results in a residue of 59 g (61%) of 1,1,3,4,4,6-hexamethyl-1,2,3,4-tetrahydronaphthalene.

We claim:
1. A process for preparing 1,1,3,4,4,6-hexamethyl-1,2,3,4-tetrahydronaphthalene of the formula I

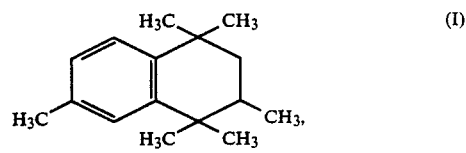

which comprises reacting p-cymene of the formula II

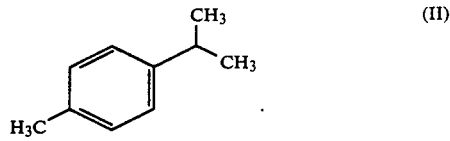

with a hexene of the formula IIIa, IIIb and/or IIIc

-continued

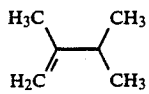 (IIIc)

in the presence of a catalytic amount of aluminum halide and a catalytic amount of a triphenylmethyl compound of the formula IV

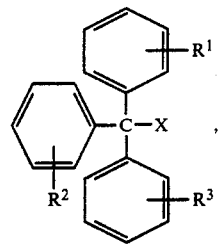 (IV)

where $R^1$, $R^2$ and $R^3$ are each, independently of one another, hydrogen, $C_1$–$C_4$-alkyl, nitro or halogen and X is hydrogen or halogen.

2. A process as claimed in claim 1, wherein the reaction is carried out at from $-10°$ C. to $50°$ C.

3. A process as claimed in claim 1, wherein p-cymene II and a hexene IIIa, IIIb or IIIc are used in a molar ratio of from 0.5:1 to 1:1.

4. A process as claimed in claim 1, wherein aluminum trichloride or tribromide is used as aluminum halide.

5. A process as claimed in claim 1, wherein aluminum trichloride or tribromide and p-cymene are used in the molar ratio of from 0.001:1 to 0.5:1.

6. A process as claimed in claim 1, wherein a triphenylmethyl compound IV and p-cymene are used in the molar ratio of from 0.001:1 to 0.1:1.

* * * * *